United States Patent
Mercier et al.

(10) Patent No.: US 9,133,415 B2
(45) Date of Patent: Sep. 15, 2015

(54) SOLID/LIQUID EXTRACTION WITH A SOLVENT COMPRISING BETWEEN 5 AND 8 CARBON ATOMS AND 1 OR 2 OXYGEN ATOMS

(75) Inventors: Eglantine Mercier, Rambouillet (FR); Jacques Legrand, Neuilly sur Eure (FR); Alex Saunois, Nogent-le-Roi (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 0 days.

(21) Appl. No.: 14/235,284

(22) PCT Filed: Jul. 30, 2012

(86) PCT No.: PCT/EP2012/064901
§ 371 (c)(1),
(2), (4) Date: Jan. 27, 2014

(87) PCT Pub. No.: WO2013/014298
PCT Pub. Date: Jan. 31, 2013

(65) Prior Publication Data
US 2014/0171669 A1   Jun. 19, 2014

(30) Foreign Application Priority Data

Jul. 28, 2011 (FR) ...................................... 11 56935

(51) Int. Cl.
| | | |
|---|---|---|
| *C11B 1/00* | (2006.01) | |
| *C12P 3/00* | (2006.01) | |
| *C11B 1/10* | (2006.01) | |
| *A23L 1/30* | (2006.01) | |
| *A23L 1/302* | (2006.01) | |
| *A61Q 19/08* | (2006.01) | |
| *A61Q 19/00* | (2006.01) | |
| *A61Q 19/06* | (2006.01) | |
| *A61K 8/97* | (2006.01) | |
| *A61K 8/99* | (2006.01) | |
| *C11B 9/02* | (2006.01) | |
| *C11B 1/04* | (2006.01) | |
| *A23D 9/00* | (2006.01) | |
| *A61K 36/48* | (2006.01) | |
| *A61K 36/54* | (2006.01) | |

(52) U.S. Cl.
CPC ... *C11B 1/10* (2013.01); *A23D 9/00* (2013.01); *A23L 1/3002* (2013.01); *A23L 1/302* (2013.01); *A23L 1/3004* (2013.01); *A61K 8/97* (2013.01); *A61K 8/99* (2013.01); *A61K 36/48* (2013.01); *A61K 36/54* (2013.01); *A61Q 19/00* (2013.01); *A61Q 19/06* (2013.01); *A61Q 19/08* (2013.01); *C11B 1/04* (2013.01); *C11B 9/025* (2013.01); *A61K 2236/00* (2013.01)

(58) Field of Classification Search
CPC ........... A23C 15/14; A23D 9/02; A23D 9/00; C11B 1/10; C11B 3/10; C11B 1/12; C11B 1/04; C11B 1/00; C11B 1/06; C11B 1/08; C11B 1/102; C11B 1/02; C11B 1/104; A23L 1/2215; A23L 1/2112; A23L 1/0152; B01D 11/0203; A23F 3/18; C12P 7/6472; C12P 7/6427; C12P 7/6463; C12P 7/6454; C07C 403/24
USPC .................. 426/417, 425; 435/134; 554/9, 20
See application file for complete search history.

(56) References Cited

U.S. PATENT DOCUMENTS

| | | | |
|---|---|---|---|
| 4,549,990 A | 10/1985 | Seguin et al. | |
| 5,679,393 A * | 10/1997 | Laur et al. | 426/417 |
| 6,759,543 B2 | 7/2004 | Bardet et al. | |

FOREIGN PATENT DOCUMENTS

| | | |
|---|---|---|
| EP | 1 246 633 A2 | 10/2002 |
| EP | 1 733 731 A1 | 12/2006 |
| EP | 1733731 A1 * | 12/2006 |
| FR | 2678632 A1 | 1/1993 |
| FR | 2762512 A1 | 10/1998 |

OTHER PUBLICATIONS

International Search Report in International Application No. PCT/EP2012/064901 mailed May 27, 2013.

* cited by examiner

*Primary Examiner* — Deborah D Carr
(74) *Attorney, Agent, or Firm* — Foley & Lardner LLP

(57) ABSTRACT

The present invention relates to a process for the solid/liquid extraction of a natural extract contained in at least one vegetable solid or micro-organism comprising at least the following steps:

solid/liquid extraction of at least one vegetable solid or micro-organism by a first solvent system comprising a solvent content chosen from the solvents comprising between 5 and 8 carbon atoms and one or two oxygen atoms in ether function, or ketone function, or ester function form, of at least 50% by volume in relation to the total volume of the first solvent system, retrieval of a natural extract, notably comprising or consisting of an oil or a butter, particularly enriched with unsaponifiable.

19 Claims, No Drawings

SOLID/LIQUID EXTRACTION WITH A SOLVENT COMPRISING BETWEEN 5 AND 8 CARBON ATOMS AND 1 OR 2 OXYGEN ATOMS

The present invention relates to a process for the solid/liquid extraction of a natural extract, notably an oil or butter, from a vegetable solid or a micro-organism, said extract, notably oil or butter, particularly comprising a high unsaponifiable content.

Unsaponifiables or unsaponifiable fractions of a fatty substance consist of compounds which, after prolonged action of an alkaline base, remain insoluble in water and can be extracted with an organic solvent.

Most vegetable oil unsaponifiables comprise major substance families. Of these major families, mention may be made of saturated or unsaturated hydrocarbons, aliphatic or terpene alcohols, sterols, tocopherols, carotenoid pigments, xanthophylls, and one or two specific families in the case of some oils.

Routine processes for obtaining unsaponifiables from vegetable oils are intended to extract all or part of the major families forming same, making it possible to prepare partial or total unsaponifiable fractions.

Partial or total unsaponifiable fractions are notably sought for the pharmacological, cosmetic and nutritional properties thereof.

Routine processes for obtaining unsaponifiables include, inter alia, a step for saponifying fat and extracting the target product (the unsaponifiable) with an organic solvent.

The solvents most commonly used for extracting oils or butters, particularly rich in unsaponifiables, from vegetable solids or micro-organisms are aliphatic solvents, and particularly hexane, and fatty acid esters, comprising more than 10 carbon atoms, and particularly methyl palmitate, methyl stearate and ethyl decanoate.

Hexane notably involves the drawback of being toxic, it is notably classified as CMR category 3 in the EU1 CMR list and in the EU2 CMR list.

Hexane further involves the drawback of being hazardous in respect of handling, notably due to the physicochemical properties thereof, particularly the flash point thereof (−23.3° C.) and/or the self-ignition temperature thereof (233.9° C.).

Fatty acid esters involve the drawback of having a high boiling point (generally over 185° C.); the removal thereof by distillation is costly in terms of energy and, due to the high temperatures required, may impair the quality of the unsaponifiable fractions extracted.

Finally, processes involving conventional aliphatic solvents, and notably hexane, may be unsatisfactory in terms of yield, in relation to the oil or butter and/or in relation to the unsaponifiable content of the oil or butter obtained, notably in terms of extraction rate of one or a plurality of particular unsaponifiable fractions, selectivity, simplicity, cost, toxicity, ecotoxicity, convenience, number of steps, notably for extraction, and/or speed.

Moreover, both in economic and environmental terms, processes for obtaining oils may require the use of quantities of organic solvents not suitable for the viability of the process, have an unsatisfactory number of extraction steps and/or be too slow.

The aim of the present invention is thus that of solving all or some of the problems mentioned above. In particular, the aim of the invention is that of providing a process having a higher overall yield, suitable for obtaining an oil or butter with a higher unsaponifiable content or having a particular profile, which is more economical, more direct, more environmentally friendly, requiring a smaller quantity of organic solvent, easier to use, quicker, generating less toxic conditions, suitable for obtaining oils or butters, notably having a high unsaponifiable content, with a yield and/or selectivity at least comparable, or even superior, to existing processes.

In particular, it is sought for the solvent(s) involved to be less toxic, notably not classified as CMR substances, notably EU2 CMR substances, and/or suitable for extracting oils or butters with a yield and/or selectivity at least comparable to the yields and selectivities obtained using conventional aliphatic solvents, notably hexane, and fatty acid esters, notably methyl stearate.

Solvents "classified as CMR substances" may be those presented in the list in the annexes of Directive 2009/2/EC of 15 Jan. 2009, this first list being referred to hereinafter as the "EU1 CMR list", those listed in the European Regulatory Classification of chemical substances that are carcinogenic, mutagenic and toxic for reproduction—31st ATP, 2009, this second list being referred to hereinafter as the "EU2 CMR list", and/or those listed in the list of "Chemicals known or suspected to cause cancer or reproductive toxicity" dated 1 Sep. 2009 issued by the "California department of public health, occupational health branch, California safe cosmetic program" associated with the "California Safe Cosmetics Act of 2005", this third list being referred to hereinafter as the "US CMR list".

When the expression EU CMR list is used herein, reference is being made to the EU1 CMR list and/or EU2 CMR list, and particularly the EU2 CMR list.

The solvents used within the scope of the present invention are thus devoid of the following solvent families and solvents:
  some alkanes, such as hexane, heptane, etc.
  some aromatic hydrocarbons, such as naphthalene,
  some halogenated solvents, notably chlorinated solvents (1,2-dichloroethane or DCE, trichloroethane, dichloromethane, trichloromethane (chloroform), dichloroethylene, carbon tetrachloride, etc.), or 1-chlorobutane.

The aim of the process according to the invention may particularly be that of enhancing the yield of natural extract, notably oil or butter, and/or the unsaponifiable content contained in this extract.

The present invention thus relates to a process for the solid/liquid extraction of a natural extract, notably comprising or consisting of an oil or a butter, particularly having a high unsaponifiable content, contained in at least one vegetable fat or micro-organism comprising at least the following steps:
  solid/liquid extraction of at least one vegetable solid or micro-organism by a first solvent system comprising a solvent content chosen from the solvents comprising between 5 and 8 carbon atoms and one or two oxygen atoms in ether function, or ketone function, or ester function form, of at least 50% by volume in relation to the total volume of the first solvent system,
  retrieval of a natural extract, notably comprising or consisting of an oil or a butter, particularly enriched with unsaponifiable.

According to the present invention, the term "natural extract" denotes a plant, mineral or animal extract.

According to the present invention, the term "solvent system" denotes a single solvent or a solvent mixture.

The term "micro-organism" denotes any microscopic living organisms, such as bacteria and/or fungi, notably yeasts and moulds.

Typically, the solid/liquid extraction is performed by contacting at least one vegetable solid and/or a micro-organisms with the first hot solvent system.

According to one particular embodiment, the solid/liquid extraction is performed using a Soxhlet. In this particular case, the solvent is advantageously heated to reflux to conduct extraction.

During the retrieval step, the natural extracts may be retrieved notably via solvent extraction, filtration and/or crystallisation.

If the first solvent system comprises a content of solvent or mixture of solvents chosen from a list of X %, this means that the additional percentage corresponds to one or a plurality of organic solvent(s) not featured in this list.

According to one particular embodiment, the first solvent system is devoid of tertbutyl ethers, particularly ETBE and/or MTBE, or terpenes, particularly limonene and alpha-pinene.

In particular, said solvent comprising between 5 and 8 carbon atoms and one or two oxygen atoms is chosen from methylketones, notably methyl isobutyl ketone or MIBK, 2-heptanone, propionates, notably ethyl propionate, n-butyl propionate, isoamyl propionate, propyl ethers, notably diisopropyl ether or DIPE, cyclic ethers, and mixtures thereof.

The CAS numbers of these various solvents are as follows: methyl isobutyl ketone or MIBK: 108-10-1; 2-heptanone: 110-43-0; ethyl propionate: 105-37-3; butyl propionate: 590-01-2; isoamyl propionate: 105-68-0; diisopropyl ether or DIPS: 108-20-3.

According to the present invention, the term "high unsaponifiable content" denotes that the oil or butter comprises at least 1% by mass, notably at least 2% by mass, and particularly at least 3% by mass of the unsaponifiable compounds initially present in the solid.

The process according to the invention may particularly be devoid of a complexing step involving the first solvent system.

The first solvent system may comprise a solvent content chosen from the solvents comprising between 5 and 8 carbon atoms and one or two oxygen atoms in ether function, or ketone function, or ester function form, particularly chosen from methylketones, notably MIBK, 2-heptanone, propionates, notably ethyl propionate, n-butyl propionate, isoamyl propionate, propyl ethers, notably DIPE, and mixtures thereof, of at least 60%, notably at least 75%, particularly at least 90%, more particularly at least 95%, even more particularly at least 99%, by volume in relation to the total volume of the first solvent system.

In particular, the first solvent system consists of solvent comprising between 5 and 8 carbon atoms and one or two oxygen atoms in ether function, or ketone function, or ester function form, particularly chosen from methylketones, notably MIBK, 2-heptanone, propionates, notably ethyl propionate, n-butyl propionate, isoamyl propionate, propyl ethers, notably DIPE, and a mixture thereof.

The first solvent system may comprise a content of solvent chosen from the solvents comprising between 5 and 8 carbon atoms and one or two oxygen atoms in ether function, or ketone function, or ester function form, particularly chosen from methylketones, notably MIBK, 2-heptanone, propionates, notably ethyl propionate, n-butyl propionate, isoamyl propionate, propyl ethers, notably PIPE, and mixtures thereof, of at least 60%, notably at least 75%, particularly at least 90%, more particularly at least 95%, even more particularly at least 99%, by volume in relation to the total volume of the first solvent system.

According to one alternative embodiment, the first solvent system consists of a solvent chosen from the solvents comprising between 5 and 8 carbon atoms and one or two oxygen atoms in ether function, or ketone function, or ester function form, particularly chosen from methylketones, notably MIBK, 2-heptanone, propionates, notably ethyl propionate, n-butyl propionate, isoamyl propionate, and propyl ethers, notably DIPE.

According to one particular embodiment, the first solvent system has a density less than 1, and notably less than or equal to 0.9.

Advantageously according to the present invention, the first solvent system further comprises hexamethyldisiloxane (HMDS), typically at a content between 0.1 and 49% by volume, in relation to the total volume of the first solvent system.

The CAS number of HMDS is 107-46-0.

According to one particular embodiment, the first solvent system may comprise:
a content of a solvent chosen from the solvents comprising at least 5 carbon atoms, particularly 5 to 8 carbon atoms, and one or two oxygen atoms in ether function, or ketone function, or ester function form, of at least 50% by volume in relation to the total volume of the first solvent system, and
HMDS, notably in a content ranging from 0.1 to 49%, more particularly from 0.5 to 30%, or even from 1 to 20%, and more particularly from 5 to 10% by volume in relation to the total volume of the first solvent system.

The first solvent system may comprise:
a content of a solvent chosen from the solvents comprising at least 5 carbon atoms, or even 5 to 8 carbon atoms, and one or two oxygen atoms in ether function, or ketone function, or ester function form, particularly chosen from methylketones, notably MIBK, 2-heptanone, propionates, notably ethyl propionate, n-butyl propionate, isoamyl propionate, propyl ethers, notably DIPE, and mixtures thereof, of at least 60%, notably at least 75%, particularly at least 90%, more particularly at least 95% by volume in relation to the total volume of the first solvent system, and
HMDS, notably in a content ranging from 0.1 to 40%, more particularly from 0.5 to 25%, or even from 1 to 20%, and more particularly from 5 to 10% by volume in relation to the total volume of the first solvent system.

In particular, the first solvent system consists of:
solvent comprising at least 5 carbon atoms, or even 5 to 8 carbon atoms, and one or two oxygen atoms in ether function, or ketone function, or ester function form, particularly chosen from methylketones, notably MIBK, 2-heptanone, propionates, notably ethyl propionate, n-butyl propionate, isoamyl propionate, propyl ethers, notably PIPE, or a mixture thereof, advantageously at a content of at least 50% by volume, in relation to the total volume of the first solvent system and
HMDS, notably in a content ranging from 0.1 to 49%, more particularly from 0.5 to 30%, or even from 1 to 20%, and more particularly from 5 to 10% by volume in relation to the total volume of the first solvent system.

The first solvent system may comprise:
a content of a solvent chosen from the solvents comprising at least 5 carbon atoms, or even 5 to 8 carbon atoms, and one or two oxygen atoms in ether function, or ketone function, or ester function form, particularly chosen from methylketones, notably MIBK, 2-heptanone, propionates, notably ethyl propionate, n-butyl propionate, isoamyl propionate, and propyl ethers, notably DIPE, of at least 60%, notably at least 75%, particularly at least 90%, more particularly at least 95% even more particularly at least 99% by volume in relation to the total volume of the first solvent system, and HMDS, notably in a content ranging from 0.1 to 40%, more particularly from 0.5 to 25%, or even from 1 to 20%, and more particularly from 5 to 10% by volume in relation to the total volume of the first solvent system.

According to one alternative embodiment, the first solvent system consists of:
- a solvent comprising at least 5 carbon atoms, or even 5 to 8 carbon atoms, and one or two oxygen atoms in ether function, or ketone function, or ester function form, particularly chosen from methylketones, notably MIBK, 2-heptanone, propionates, notably ethyl propionate, n-butyl propionate, isoamyl propionate, and propyl ethers, notably DIPE, advantageously at a content of at least 50% by volume, in relation to the total volume of the first solvent system, and
- HMDS, notably in a content ranging from 0.1 to 49%, more particularly from 0.5 to 25%, or even from 1 to 20%, and more particularly from 5 to 10% by volume in relation to the total volume of the first solvent system.

According to one particular embodiment, the first solvent system comprises a content of CMR solvent(s), particularly featuring in the EU1, EU2, and/or US CMR list, less than or equal to 10%, notably less than or equal to 5%, particularly less than or equal to 2%, more particularly less than or equal to 1%, even more particularly less than or equal to 0.5%, or even less than or equal to 0.1% by volume in relation to the total volume of the first solvent system.

Even more particularly, the first solvent system is devoid of solvents featuring in the EU1, EU2 and/or US CMR list, and more particularly hexane and dichloroethane.

The solvents used in the first solvent system have a purity of at least 90%, notably at least 95%, particularly at least 98%, more particularly at least 99%, or even at least 99.5%.

The invention also relates to a process for obtaining an unsaponifiable fraction, notably a total or partial fraction, comprising at least the following steps:
- solid/liquid extraction of at least one vegetable solid or micro-organism by a first solvent system comprising a solvent content chosen from the solvents comprising between 5 and 8 carbon atoms and one or two oxygen atoms in ether function, or ketone function, or ester function form, particularly chosen from methylketones, notably MIBK, 2-heptanone, propionates, notably ethyl propionate, n-butyl propionate, isoamyl propionate, propyl ethers, notably DIPE, and mixtures thereof, of at least 50% by volume in relation to the total volume of the first solvent system,
- advantageously retrieval of a natural extract enriched with oil or butter, particularly in the form of an organic solution enriched with oil or butter, or even retrieval of the oil or butter, notably said natural extract enriched with unsaponifiable,
- conversion of said oil or said butter into hydro-alcoholic solution, via a saponification step,
- extraction of the hydro-alcoholic solution wherein the fatty fraction is separated from the unsaponifiable fraction by liquid/liquid extraction, and
- retrieval of the unsaponifiable fraction, notably a partial or total fraction.

According to the present invention, the term "total fraction" denotes that the fraction comprises all the families of substances forming the unsaponifiable contained in the vegetable oil or butter or in the micro-organism in question.

According to the present invention, the term "partial fraction" denotes that the fraction comprises at least one of the families of substances forming the unsaponifiable contained in the vegetable oil or butter or in the micro-organism in question.

The first solvent system is as defined for the process for the solid/liquid extraction of a plant extract.

Particularly advantageously, the solid/liquid extraction solvents according to the invention comprise between 5 and 8 carbon atoms, and thus have small carbon chains; they thus have the advantage of being sufficiently lipophilic to extract an oil and/or butter and the unsaponifiable fractions contained therein and to be suitable for being subsequently readily separated from the extract obtained.

The conversion of said natural extract, notably of said oil or said butter, into hydro-alcoholic solution may be performed in a conventional solvent system.

According to one particular alternative embodiment, the conversion of said natural extract, notably of said oil or said butter, into hydro-alcoholic solution may be performed in a second solvent system comprising, or even consisting of, at least one solvent from the first solvent system.

More particularly, the conversion may be performed without total purification of said natural extract, notably of the oil or butter. Particularly, the conversion is performed directly on the basis of the organic solution enriched with said natural extract, notably with oil or butter, notably comprising at least 2% by mass, particularly at least 5% by mass, or even at least 10% by mass of oil or butter in relation to the total mass of the organic solution enriched with oil or butter.

According to a first alternative embodiment, the conversion is performed on a fraction, notably partially evaporated, to which less than 50% by mass of other solvents is added, or even no other solvent are added.

According to a further alternative embodiment, at least 10% of at least one other solvent, such as C2 to C4 alcohols, notably ethanol, n-propanol, iso-propanol, butanol, particularly n-butanol, methyltetrahydrofuran (MeTHF) and mixtures thereof, may be added to the organic solution enriched with oil or butter, notably evaporated.

When the hydro-alcoholic solution is extracted by liquid/liquid extraction, this may be performed with a third solvent system defined in the same way as the first solvent system. In particular, this third solvent system comprises, or even consists of, the same solvents as those used in the first and/or second solvent system.

As a general rule, the process for the solid/liquid extraction according to the invention may be more economical, more direct, more environmentally friendly, requiring a smaller quantity of organic solvent, easier to use, quicker, generating less toxic conditions, suitable for obtaining oils or butters, notably having a high unsaponifiable content, with a yield and/or selectivity at least comparable, or even superior, to existing processes.

The saponification and unsaponifiable extraction part may notably be performed according to the procedures described in EP 1 246 633.

The vegetable solid or the micro-organisms used in the present processes may be obtained from soybean, rape, corn, sunflower, sesame, lupin, cotton, coconut, olive, avocado, cocoa, illipe, shea, palm kernel, peanut, copra, linseed, castor, grape seeds, squash seeds, blackcurrant seeds, melon seeds, tomato seeds, pumpkin seeds, almond, hazelnut, walnut, evening primrose, borage, safflower, camelina, poppy, macroalgae, microalgae, such as Haematococcus, Dunaliella, Spirulina, Chorella, and/or micro-organisms, notably marine, fresh water or terrestrial micro-organisms, particularly yeasts, moulds, and more particularly, bacteria, and mixtures thereof.

Typically, the unsaponifiable fraction contents obtained range from 2 to 10% in avocado oil, are approximately 0.5% in coconut oil, approximately 1% in soybean oil and approximately 1% in olive oil.

Those skilled in the art know the processes to be used to extract the unsaponifiable fraction of a vegetable oil or butter or a micro-organism and know how to apply same to the conversion, extraction and/or retrieval part of the unsaponifiable according to the present invention.

Of the prior art relating to this part, particular mention may be made of the process for preparing avocado oil unsaponifiable as described and claimed in the patent FR 2 678 632.

In this way, the avocado oil unsaponifiable can be prepared from the previously heat treated fruit, before extraction of the oil and saponification, as described in the patent FR 2 678 632.

This heat treatment consists of controlled drying of the fruit, which is preferably fresh, for at least four hours, advantageously at least 10 hours, preferably between approximately 24 and approximately hours, at a temperature preferably of at least approximately 80° C. and preferably between approximately 80 and approximately 120° C.

Mention may also be made of the process for preparing soybean oil unsaponifiable, obtained from a soybean oil unsaponifiable concentrate.

Said unsaponifiable concentrate may be prepared by means of molecular distillation according to a process as described for lupin oil in the patent application FR 2 762 512, but suitable for soybean oil.

In this process, the soybean oil is distilled in a centrifugal or wiped-film type molecular still, at a temperature between approximately 210 and 250° C. and in a high vacuum, between 0.01 and 0.001 millimetres of mercury (i.e. 0.13 to 1.3 Pa).

The distillate obtained has an unsaponifiable content between 5 and 40% by mass and thus forms a soybean unsaponifiable concentrate.

The concentrate is then saponified with a base such as potash or soda in a polar, notably alcoholic, medium, preferably ethanol, n-propanol, iso-propanol, butanol, particularly n-butanol, methyl-tetrahydrofuran (MeTHF), or a mixture thereof, and it is subjected to one or a plurality of extractions with the third solvent system.

The extraction solution obtained is preferably subsequently centrifuged, filtered and washed with water to remove residual traces of alkalinity.

The extraction solvent is evaporated thoroughly to retrieve the unsaponifiable. It is also obviously possible to envisage further operations known to those skilled in the art, such as an odour removal step.

Finally, prior to the saponification thereof, the natural extract, notably the oil or butter, may be previously enriched with unsaponifiable by separating a majority of the constituents of the unsaponifiable retrieved in a concentrate. Various methods may be used: cold crystallisation, liquid/liquid extraction, or molecular distillation.

The prior concentration of the oil or butter in respect of unsaponifiable makes it possible to reduce the volumes of natural extract, notably oil or butter, to be saponified.

Molecular distillation is particularly preferred, being performed preferably at a temperature between approximately 180 and approximately 230° C. by maintaining a pressure between $10^{-3}$ and $10^{-2}$ mm Hg and preferably in the region of $10^{-3}$ mm Hg.

The unsaponifiable concentration of the distillate may be up to 60% by mass in relation to the total mass.

More particularly, the present invention relates to a process as described in the present description wherein the unsaponifiable obtained is chosen from a soybean unsaponifiable, advantageously enriched with sterols, tocopherols, and/or squalene, an avocado unsaponifiable, notably an avocado unsaponifiable enriched with furan fraction and/or an avocado unsaponifiable enriched with sterol fraction and/or an avocado unsaponifiable enriched with trihydroxylated compounds.

The present invention further relates to an oil or butter devoid of solvents classified in the EU1 CMR list, EU2 and/or US CMR list, in particular said oil or said butter is suitable for being obtained, or directly obtained, by means of the process according to the invention.

The present invention further relates to an unsaponifiable fraction, notably a partial or total fraction, devoid of solvents classified in the EU1, EU2 and/or US CMR list, in particular said fraction is obtained by means of the process according to the invention.

The present invention further relates to the use of this fraction, this natural extract, this butter or this oil for preparing a composition, notably a pharmaceutical, nutritional and/or cosmetic composition, or a nutritional supplement.

The present invention also relates to the unsaponifiable fraction, notably partial or total fraction, the oil or butter, devoid of solvents classified in the EU1, EU2 and/or US CMR list, as described above, for the use thereof as a medicinal product, as a medical device, as a dermatological agent, as a cosmetic agent, or as a nutraceutical, intended for humans or animals, advantageously for preventing and/or treating connective tissue disorders such as arthrosis, joint diseases such as rheumatism, periodontal diseases, such as gingivitis or periodontitis, or for preventing and/or treating disorders of the dermis and/or hypodermis such as skin ageing, stretch marks and cellulite, or epidermal barrier disorders such as skin inflammations, atopic eczema and irritant and/or inflammatory dermatitis.

The present invention further relates to a composition, notably a nutritional, cosmetic or pharmaceutical composition, or a nutritional supplement, comprising a natural extract, an oil, a butter or an unsaponifiable fraction of at least one natural extract, vegetable oil or butter or a micro-organism, said extract, oil, butter or fraction being devoid of solvents classified in the EU1, EU2 and/or US CMR list, and/or said extract, oil, butter or fraction is suitable for being obtained, or directly obtained, by means of the process according to the invention, and said composition optionally comprising an excipient, particularly acceptable in cosmetological, nutritional or pharmaceutical terms.

According to one particular embodiment, the present invention relates to a composition, notably a nutritional, cosmetic or pharmaceutical composition, or a nutritional supplement, comprising at least one unsaponifiable, particularly a soybean unsaponifiable, an avocado unsaponifiable, more particularly notably an avocado unsaponifiable enriched with furan fraction and/or an avocado unsaponifiable enriched with sterol fraction, suitable for being obtained or directly obtained by means of the process according to the invention.

The pharmaceutical, nutritional compositions, or nutritional supplements, may be intended to prevent and/or treat connective tissue disorders, notably arthrosis, periodontal disease, skin ageing and/or skin inflammations.

The pharmaceutical or cosmetic compositions according to the invention may be intended to prevent and/or treat skin disorders of the epidermis, dermis and/or hypodermis.

According to the present invention, the term "devoid of solvents classified in the EU1, EU2 and/or US CMR list"

denotes a total content of solvents classified in the EU1, EU2 and/or US CMR less than 10 ppm, notably less than 5 ppm, particularly less than 2 ppm, or even less than 1 ppm.

The present invention further relates to a cosmetic treatment process such that the cosmetic composition according to the invention is applied topically.

The invention also relates to a plant extract, an oil, a butter, or an unsaponifiable of a vegetable oil or butter or a microorganism obtained or suitable for being obtained according to the present invention for the use thereof as a medicinal product, particularly intended to treat or prevent connective tissue disorders, and notably arthrosis.

According to a further aspect, the invention relates to the use of HMDS, with a content ranging from 0.1 to 49%, typically from 0.1 to 45%, by volume in relation to the total volume of the extraction solvents or extraction systems, in a process for the solid/liquid extraction notably of unsaponifiables, advantageously from a vegetable solid or a microorganism.

HMDS may be present at a content ranging from 0.5 to 25%, or even from 1 to 20%, and more particularly from 5 to 10% by volume in relation to the total solvent volume.

In particular, said process comprises a solvent system comprising:
- at least one solvent comprising at least 5 carbon atoms, or even 5 to 8 carbon atoms, and one or two oxygen atoms in ether, ketone or ether function form, particularly at least one solvent chosen from
  - methylketones, notably MIBK, 2-heptanone,
  - propionates, notably ethyl propionate, n-butyl propionate, isoamyl propionate,
  - propyl ethers, notably DIPE,
  - a mixture thereof, or
- at least one solvent chosen from
  - fluorinated aromatic solvents, notably trifluorotoluene (BTF) and hexafluorobenzene (BHF),
  - tert-butyl ethers, notably 2-ethoxy-2-methylpropane, also referred to ethyl-tert-butyl-ether (ETBE), and 2-methoxy-2-methylpropane, also referred to as methyl-tert-butyl-ether (MTBE),
  - solvents comprising at least one silicon atom, notably hexamethyldisiloxane (HMDS) and tetramethylsilane (TMS),
  - methyl-tetrahydrofuran (MeTHF), and
  - mixtures thereof, or
- a mixture of the above solvents.

The content of these solvents may be as described above.

The CAS number of these various solvents are as follows BTF: 98-08-8; BHF: 392-56-3; ETBE: 637-92-3; MTBE: 1634-04-4; TMS: 75-76-3; and MeTHF: 96-47-9.

The presence of HMDS among the extraction solvents may be suitable for refining the profile of the unsaponifiable obtained, enhancing the extraction rate of one or more fractions, and/or the overall extraction yield.

HMDS may notably be suitable for modulating the extraction capacity of the solvent system. In this way, the presence of HMDS among the extraction solvents may be suitable for enhancing the oil yield and/or be suitable for enhancing the unsaponifiable content in this oil, refining the profile of the unsaponifiable obtained and/or the extraction rate of one or more fractions.

Moreover, the presence of HMDS in a content as defined above in the solvent system may be suitable for reducing solvent consumption and/or extraction times.

In this way, HMDS may be used as an agent for enhancing the extraction yield, an agent for enhancing the unsaponifiable content of the natural extract, and/or an acceleration agent.

Obviously, the various features disclosed in the present description may be combined together.

By way of examples illustrating the present invention, the following experiments were performed.

EXAMPLES

In all the examples, a reference test using hexane was performed.

Example 1

Extraction Using Dried Avocadoes

Extraction of dried avocadoes was performed with hexane (reference) and with the following solvents: 2-heptanone, MIBK and ethyl propionate.

Dried avocado is ground and introduced into a cellulose cartridge (30 to 40 g). The extraction is performed in a Soxhlet type apparatus (BUCHI B-811). Four extractions are then run in parallel, each corresponding to 20 extraction/siphoning cycles. Once the extraction has been finalised, the extraction solvent is evaporated and the desolventised residue is weighed. The mass yields are then compared. The results are shown in Table 1.

TABLE 1

| Extraction solvent | Mass extraction yield (% m/m) | Unsaponifiable content of natural extract (% m/m) | Increase in unsaponifiable content of natural extract (%) |
|---|---|---|---|
| Hexane | 58.0 | 4.12 | 0 |
| 2-heptanone | 58.4 | 4.20 | +1.9 |
| MIBK | 58.4 | 4.49 | +9.0 |
| ethyl propionate | 58.5 | 4.51 | +9.5 |

The mass extraction yield is equivalent to:

$R = 100 \times (\text{extract mass/mass of solid used})$

The unsaponifiable content of the natural extract is calculated by means of gas chromatography.

The increase in the unsaponifiable content of the natural extract is calculated as follows:

$A = 100 \times (\text{unsaponifiable content of the natural extract obtained with the solvent } S - \text{unsaponifiable content of the natural extract obtained with hexane}) / \text{unsaponifiable content of the natural extract obtained with hexane.}$ These results demonstrate that the solvents according to the present invention have extraction yields which are equivalent or even superior to those of hexane. In any case, the unsaponifiable content of the natural extract obtained is greater than that of the reference natural extract obtained with hexane, the increase varying from 1.9 to 9.5%.

Example 2

Extraction from Ground Lupin Hulls

Extraction of ground lupin hulls was performed according to the method in Example 1 and with the following solvents:

2-heptanone, MIBK, ethyl propionate and isopropylether. The results are shown in Table 2.

TABLE 2

| Extraction solvent | Mass extraction yield (% m/m) | Increase in mass extraction yield (% m/m) | Unsaponifiable content of natural extract (% m/m) | Unsaponifiable extraction rate per 100 g of solid (%) |
|---|---|---|---|---|
| Hexane | 0.93 | 0 | 29.1 | 0.27 |
| 2-heptanone | 1.43 | 53.8 | 18.2 | 0.26 |
| MIBK | 1.17 | 25.8 | 25.3 | 0.30 |
| ethyl propionate | 1.03 | 10.8 | 34.0 | 0.35 |
| Isopropyl-ether | 0.99 | 6.5 | 19.4 | 0.19 |

The mass extraction yield is equivalent to:

$$R = 100 \times (\text{extract mass/mass of solid used})$$

The increase in the mass extraction yield is calculated as follows:

$$A' = 100 \times (\text{mass extraction yield obtained with the solvent } S - \text{mass extraction yield obtained with hexane})/\text{mass extraction yield obtained with hexane}$$

The unsaponifiable content of the natural extract is evaluated by means of gas chromatography.

The unsaponifiable extraction rate per 100 g of solid is calculated as follows:

$$T = (\text{mass extraction yield} \times \text{unsaponifiable content})/100$$

These results demonstrate that the solvents according to the present invention are suitable for enhancing the mass extraction yield in relation to that of hexane, the increase in the mass extraction yield ranging from 6.5% with DIPE to 53.8% with 2-heptanone.

With the exception of DIPE, the unsaponifiable extraction rates per 100 g used are equivalent to those obtained with hexane.

Example 3

Extraction Using Lupin Seed Meal

Extraction with lupin seed meal was performed with hexane (reference) and with MIBK.

60 g of lupin seed meal is introduced into a cellulose cartridge. The extraction is performed in a Soxhlet type apparatus (BUCHI B-811). Four extractions, two per solvent, are then run in parallel; each corresponds to 20 extraction/siphoning cycles. Once the extraction has been finalised, the extraction solvent is evaporated and the desolventised residue is weighed. The mass yields are then compared. The unsaponifiable composition of the oils is then analysed. The mean results are shown in Table 3.

TABLE 3

| Extraction solvent | Mass extraction yield (% m/m) | Carotenoid content of natural extract (mg/100 g of oil) | Increase in carotenoid content of natural extract (%) |
|---|---|---|---|
| Hexane | 12.5% | 24.9 | 0 |
| MIBK | 13.0% | 37.8 | +51.8% |

MIBK, a non-CMR solvent, is suitable for increasing the oil extraction yield by 0.5%. MIBK, in addition to a low toxicity, offers the advantage of increasing the extraction rate in respect of a particular unsaponifiable fraction, carotenoids, by almost 52% by mass, highlighting the low degradation of this family of compounds during the extraction step.

The invention claimed is:

1. A process for solid/liquid extraction of a natural extract contained in at least one vegetable solid or micro-organism, comprising at least the following steps:
    solid/liquid extraction of at least one vegetable solid or micro-organism by a first solvent system comprising a solvent content selected from solvents comprising between 5 and 8 carbon atoms and one or two oxygen atoms in ether function, or ketone function, or ester function form, of at least 50% by volume in relation to the total volume of the first solvent system,
    retrieving a natural extract comprising an oil or a butter, wherein the solvent comprising between 5 and 8 carbon atoms and one or two oxygen atoms is selected from methylketones, propionates, propyl ethers, and mixtures thereof.

2. A process according to claim 1, for obtaining a total or partial unsaponifiable fraction, further comprising the following steps:
    converting said natural extract into hydro-alcoholic solution, via a saponification step,
    extracting the hydro-alcoholic solution wherein the fatty fraction is separated from the unsaponifiable fraction by liquid/liquid extraction, and
    retrieving the unsaponifiable fraction.

3. A process according to claim 1, wherein the first solvent system has a density less than 1.

4. A process according to claim 1, wherein the first solvent system comprises a content of a solvent selected from the solvents comprising between 5 and 8 carbon atoms and one or two oxygen atoms in ether function, or ketone function, or ester function form selected from methylketones, propionates, propyl ethers, and mixtures thereof, of at least 75% by volume in relation to the total volume of the first solvent system.

5. A process according to 1, wherein the first solvent system further comprises hexamethyldisiloxane (HMDS) at a content between 0.1 and 49% by volume in relation to the total volume of the first solvent system.

6. A process according to claim 1, wherein the first solvent system comprises a content of CMR solvent(s) featuring in the EU1, EU2, and/or US CMR list less than or equal to 0.1%, by volume in relation to the total volume of the first solvent system.

7. A process according to claim 2, wherein the conversion of said natural extract into hydro-alcoholic solution is performed in a second solvent system comprising at least one solvent selected from C2 to C4 alcohols, 2-methyltetrahydrofuran (MeTHF) and mixtures thereof, of at least 10% by volume in relation to the total volume of the second solvent system, said second solvent system being suitable for being added to the organic solution enriched with oil or butter.

8. A process according to claim 2, wherein the conversion of said natural extract into hydro-alcoholic solution is performed in a second solvent system comprising or consisting of at least one solvent from the first solvent system.

9. A process according to claim 2, wherein the conversion is performed directly on the basis of the organic solution enriched with oil or butter comprising at least 2% by mass of oil or butter in relation to the total mass of the organic solution enriched with oil or butter.

10. A process according to claim 9, wherein the conversion is performed on an organic solution enriched with oil or butter, totally or partially evaporated.

11. A process according to claim 2, wherein the hydroalcoholic solution is extracted by liquid/liquid extraction performed with a third solvent system comprising all or some of the same solvents as those used in the first and/or second solvent system.

12. A process according to claim 1, wherein the unsaponifiable obtained is selected from a soybean unsaponifiable, an avocado unsaponifiable, and a mixture of avocado and soybean unsaponifiables (ASU).

13. A process, comprising solid/liquid extraction of at least one vegetable solid or micro-organism using a solvent system comprising hexamethyldisiloxane (HMDS) at a content ranging from 0.1 to 49% by volume in relation to the total volume of the extraction solvents.

14. A process according to claim 1, wherein said natural extract comprising an oil or a butter is enriched with unsaponifiable.

15. A process according to claim 1, wherein the solvent comprising between 5 and 8 carbon atoms and one or two oxygen atoms is selected from methyl isobutyl ketone (MIBK), 2-heptanone, ethyl propionate, n-butyl propionate, isoamyl propionate, diisopropyl ether (DIPE), and mixtures thereof.

16. A process according to claim 4, wherein the first solvent system comprises a content of a solvent selected from the solvents comprising between 5 and 8 carbon atoms and one or two oxygen atoms in ether function, or ketone function, or ester function form selected from methylketones, propionates, propyl ethers, and mixtures thereof, of at least 90% by volume in relation to the total volume of the first solvent system.

17. A process according to claim 12, wherein the unsaponifiable obtained is selected from an avocado unsaponifiable enriched with furan fraction, an avocado unsaponifiable enriched with sterol fraction, and a mixture thereof.

18. A process according to claim 10, wherein the conversion is performed by adding less than 50% by mass of other solvents in relation to the total mass of the organic solution enriched with oil or butter.

19. A process according to claim 7, wherein the second solvent system comprises at least one solvent selected from ethanol, n-propanol, iso-propanol, butanol, 2-methyltetrahydrofuran (MeTHF), and mixtures thereof.

* * * * *